United States Patent

Sakamoto et al.

Patent Number: 5,705,393
Date of Patent: Jan. 6, 1998

[54] REAGENT COMPOSITION FOR MEASUREMENT OF IONIC STRENGTH OF LIQUID SAMPLES

[75] Inventors: Hisashi Sakamoto; Toshihisa Inoue; Kaori Kurata, all of Kyoto, Japan

[73] Assignee: Kyoto Daiichi Kagaku Co., Ltd., Kyoto-Fu, Japan

[21] Appl. No.: 722,778

[22] Filed: Sep. 27, 1996

[30] Foreign Application Priority Data

Oct. 17, 1995 [JP] Japan .................................. 7-268484

[51] Int. Cl.⁶ ........................................ G01N 31/22
[52] U.S. Cl. .............................. 436/2; 422/61; 73/32 R
[58] Field of Search ....................... 436/2; 422/58, 422/61; 73/30.01–30.04, 32 R; 137/91; 210/740, 743; 110/84

*Primary Examiner*—Lyle A. Alexander
*Attorney, Agent, or Firm*—Jones & Askew

[57] ABSTRACT

The present invention provides a reagent composition for measurement of ionic strength of liquid samples (especially for measurement of specific gravity of urine), which contains at least one phosphoric diester, at least one pH buffering agent, and at least one pH indicator. The present invention also provides a test tool containing the reagent composition which may be a test strip made by impregnation, coating, or printing of the composition. The reagent composition and the test tool are convenient and less susceptible to pH and temperature of the samples, measurement timing, etc. The compounds shown by the following general formula (1):

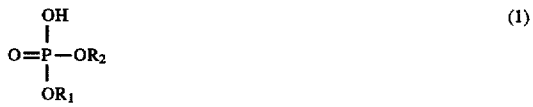

wherein $R_1$ and $R_2$ in the formula (1) represent straight or branched alkyl groups containing 4–20 carbon atoms, phenyl groups which may be substituted, benzyl groups which may be substituted, or groups containing polyalkylene glycol chains, are preferable as a phosphoric diester.

6 Claims, No Drawings

REAGENT COMPOSITION FOR MEASUREMENT OF IONIC STRENGTH OF LIQUID SAMPLES

BACKGROUND OF THE INVENTION

1. Field of the Invention

The present invention relates to a reagent composition for measurement of ionic strength of liquid samples, and to a test strip prepared by impregnation, coating, or printing of the reagent composition. The present invention is particularly useful for reagent compositions or test tools for measurement of specific gravity of biological liquids, especially urine which exhibit well correlation between ionic strength and specific gravity.

2. Description of the Related Art

Measurement of specific gravity of liquid samples is carried out in the wide variety of technical fields. Especially, measurement of specific gravity of urine is one of the most important items with clinical significance in the field of clinical tests and utilized for diagnosis of renal diseases, etc. Specific gravity of urine of healthy individuals ranges widely from 1.005 to 1.030 in general, and it amounts to about 1.015 for 24-hour accumulated urine. General methods currently utilized to measure specific gravity of urine directly include those using a urinometer (floating weight method), picno-meter, or refractometer.

Although most of these methods provide required accuracy, these apparatus require maintenance such as scale calibration or washing and management of tools, to keep accuracy. It takes much time and labor, and thus they suffer from many inconveniences. Urinometers require urine sample in a volume exceeding a specified quantity at the time of measurement, and an insufficient volume of urine may cause difficulty in measurement. In addition, there is such a shortcoming that bubbles on the liquid surface or capillary reaction may make it difficult to read scales.

A method using test strips to measure specific gravity of urine in a form of test paper has been developed in order to solve these problems and has become widely utilized. According to this method, measurement is easily carried out by a dip-and-read method in which a test strip is immersed in urine and the color developed is compared with a color list. In addition, this test strip can be used in combination with test strips for other urine test items, such as glucose, ketone body, protein, hemoglobin, leukocytes, bilirubin, urobilinogen, pH, and ascorbic acid to allow simultaneous measurement. Thus, this method is very convenient.

In recent years, various methods for indirect measurement of specific gravity through measuring ionic strength of liquid samples have been proposed as methods to obtain specific gravity of liquid samples by colorimetric analysis using such test strips. It is known that ionic strength and specific gravity are well correlated and proportional, especially in urine. The relationship between ionic strength and specific gravity of liquid samples is described in detail in Japanese Examined Patent Publication No. JP-B-62-12858 (Japanese Unexamined Patent Publication No. JP-A-55-101047) and thus not further mentioned in this specification.

As methods to obtain specific gravity by measuring ionic strength, for example, the followings have been proposed: a method wherein when microcapsules containing a colorant kept in carrier matrix contact with a solution with a low osmotic pressure, the pressure inside the microcapsules is elevated so that the microcapsules are swollen to collapse and the colorant is eluted to change a color of the matrix (darkness of color is proportional to specific gravity) (Japanese Examined Patent Publication No. JP-B-60-46374); a method wherein ionic strength or specific gravity is measured using a test strip containing a composition comprising a polyelectrolyte neutralized at least about 50%, such as polyacrylic acid or polyvinyl amine, and pH indicators (Japanese Unexamined Patent Publication No. JP-A-55-101047); a method using a composition comprising a strongly acidic or basic polyelectrolyte, a buffering substance which can maintain pH at least about 5.5, and pH indicating means, wherein the polyelectrolyte is polystyrene sulphonate, polyvinyl sulfate, or polyvinyl ammonium chloride (Japanese Unexamined Patent Publication No. JP-A-56-21064); a method using a reagent containing a weakly basic polyelectrolyte polymer neutralized with strong organic acid and indicators, wherein polyethylene imine, polyvinyl amine, polyaminostyrene or copolymers of the monomers constituting the above polymers is used as the polyelectrolyte polymer (Japanese Unexamined Patent Publication No. JP-A-59-133207); a method using a composition containing a weakly basic polyelectrolyte polymer in which at least one carboxyl group is present in a form of ammonium salt, and indicators (Japanese Unexamined Patent Publication No. JP-A-59-133208); a method using a composition which contains at least one pH buffering agent but does not contain polyelectrolyte polymer, or contains at least one pH buffering agent and/or at least one complex forming agent, and both of the compositions further contain at least one pH indicator (Japanese Unexamined Patent Publication No. JP-A-2-66451); a method using a composition containing at least one detergent and at least one pH indicator (Japanese Unexamined Patent Publication No. JP-A-5-172822); and a method using a composition containing at least one pH buffering agent, at least one pH indicator and at least one surfactant as a sensitizer (Japanese Unexamined Patent Publication No. JP-A-5-196616).

In the conventional colorimetric methods to measure specific gravity of liquid samples through measurement of ionic strength as described in the publications above, test strips using electrolyte polymers, complex forming agents, pH buffering agents, pH indicators, microcapsules, etc., are used. However, since these methods are susceptible to influence of, for example, pH and temperature of liquid samples, measurement timing, etc., accurate measurement is difficult. Further, the test strips used in the conventional colorimetric measurement methods are generally difficult to be manufactured and not practical.

SUMMARY OF THE INVENTION

In view of the above, an object of the present invention is to provide a reagent composition and a test tool for measurement of ionic strength which is proportional to specific gravity of liquid samples, thereby to obtain specific gravity, which are more convenient and less susceptible to pH and temperature of liquid samples, measurement timing, etc., as compared with conventional methods.

The present inventors have found out that the use of ion exchange potential of phosphoric diesters provides more convenient test tools which are not affected by pH and temperature of liquid samples, measurement timing, etc.

Therefore, the present invention relates to a reagent composition for measurement of ionic strength of liquid samples which contains at least one phosphoric diester, at least one pH buffering agent, and at least one pH indicators.

The present invention also relates to a test tool which contains the above-mentioned reagent composition, and especially a test strip according to the present invention can be prepared by impregnation of said reagent composition into absorptive carrier, or coating or printing of said reagent composition on a film.

A preferable phosphoric diester used in the present invention is those represented by the general formula (1):

wherein, $R_1$ and $R_2$ in the formula (1), which may be different or the same each other, are organic groups selected from a group consisting of (a) straight or branched alkyl groups containing 4–20 carbon atoms, (b) phenyl groups, (c) phenyl groups substituted by straight or branched alkyl or alkoxyl groups, (d) benzyl groups, (e) benzyl groups substituted by straight or branched alkyl or alkoxyl groups, and (f) groups represented by the following formula(2):

wherein, $R_3$ in the formula (2) is an organic group selected from a group consisting of any of the groups (a)–(e) shown for the formula (1) above, straight or branched alkylester residues and phenyl ester residues. m represents 2–6, and n represents an integer 1 or higher.

Further, the straight or branched alkyl or alkoxyl groups introduced in said phenyl or benzyl groups preferably contain about 1–20 carbon atoms.

The phosphoric diester of the present invention is generally called as a liquid ion exchanger and is characterized by that it has both an ion exchange group and a large non-polar region as shown in the formula (1), that is, it is not dissolved in aqueous phases. Therefore, it can reach exchange equilibrium quickly and the extraction efficiency is high due to the insolubility in aqueous phases. Although the phosphoric diester of the present invention was originally developed for the purpose of purification and recovery of nuclear fuel substances, it has also been applied to general separation and analysis recently.

For example, extraction of sodium and calcium with the phosphoric diester is represented by the equation below. The following reactions:

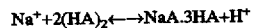

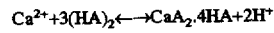

(wherein HA represents acids) occurs in diluted solutions, while simple salts such as NaA and $CaA_2$ are generated and association and extraction of water occur as follows:

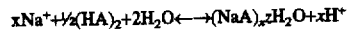

when a concentration is elevated.

The above-mentioned reactions are described in "Surfactants: Physical Properties, Application, and Chemical Ecology," Kitahara, F., Tamai, Y., Hayano, S. and Hara, I., ed., pp. 415–421.

Unexpectedly, excellent results were obtained in the present invention, when the present inventors investigated whether or not the phosphoric diester effective for extraction of such metal ions can be applied to measurement of ionic strength of liquid samples. That is, when the phosphoric diester generates an ion exchange reaction according to the metal ion concentration of liquid samples, color can be changed by a pH indicator responding to the ion exchange.

As liquid samples subjected to measurement according to the present invention, aqueous liquids, for example, biological liquids such as urine, blood, and sweat, and industrial effluent can be mentioned. Especially, the reagent composition and the test tool according to the present invention are useful for the measurement of specific gravity of urine, in which ionic strength and specific gravity are well correlated.

The test tool using the reagent composition of the present invention has especially high sensitivity with high reaction rates, providing homogenous color development.

DESCRIPTION OF THE PREFERRED EMBODIMENTS

Embodiments of the present invention will be described below.

Specific examples of the phosphoric diester according to the present invention include di(ethylhexyl)phosphate, di(hexadecyl)phosphate, di(polyethyleneglycol-4-nonylphenyl)phosphate, dibenzyl phosphate, di-n-butyl phosphate, diphenyl phosphate, etc. Among them, di(ethylhexyl)phosphate is particularly preferable. Preferably, the concentration of the phosphoric diester in the reagent composition is about 0.01–1.0M.

As the pH buffering agent of the present invention, organic bases or combinations of organic bases and acids are suitable. Preferably, buffers used in the pH range between 3.0 and 10.0 are employed. Specifically, 2-amino-2-methylpropane-1,3-diol, Tris buffers, various Good buffers, or buffer solutions combined these buffers with hydrochloric acid, etc., can be mentioned. The concentration of the pH buffering agent in the reagent composition is preferably about 0.01–2M.

The pH indicator of the present invention may be selected from any indicators whose transition interval are within a pH fluctuation zone of the above-mentioned pH buffering agent. Especially, triphenylmethane pH indicators in which dissociation is accelerated by an increase in ionic strength can be mentioned as preferred ones. Bromothymol Blue, Bromocresol Purple, Thymol Blue, Phenol Red, Bromocresol Green, etc., can be specifically mentioned. These indicators may be used alone or in combination. The concentration of the pH indicator in the reagent compositions is preferably in a range of 0.001–1.0 w/v %.

When a total amount of the three components, phosphoric diester, pH buffering agent, and pH indicator in the reagent composition of the present invention is presumed to be 100% (w/w), the preferable content of the phosphoric diester is 20–80% (w/w), more preferably 30–60% (w/w), that of the pH indicator 0.01–30% (w/w), more preferably 0.05–10% (w/w), and that of the pH buffering agent 30–80% (w/w), more preferably 40–60% (w/w).

The reagent composition of the present invention may contain known components to be blended such as binders, for example, polyvinyl pyrrolidone, hydroxyprophyl methylcellulose, polyvinyl alcohols, etc., in addition to the three components mentioned above.

The test tool of the present invention may be whatever containing the reagent composition of the present invention mentioned above, without any restriction. It may take any forms, for example, a test strip holding the reagent composition on a suitable support, a solution containing the reagent composition dissolved in a solvent, powders containing the reagent composition, a tablet in which the reagent composition is enclosed, and so on.

When the reagent composition of the present invention is used in a test strip, the test strip can be obtained by firstly impregnating the reagent composition of the present invention into absorptive carrier such as filter paper, or coating or printing mixture of the reagent composition with polymer and the like on a film, and then drying sufficiently. The test strip thus obtained is then immersed in a liquid sample to be detected, removed from the sample, and stood for a certain period of time. After that, a variation of pH of the test tool mentioned above and that of a degree of dissociation of the pH indicator are detected.

As absorptive carriers, paper such as filter paper, porous membrane of synthetic resins such as polystyrene, nonwoven cloth and so on, can be mentioned. Plates of plastics such as polyvinyl chloride, polyethylene terephthalate film and so on, can be mentioned as films to be coated or printed.

Variation of pH or that of a degree of dissociation of the pH indicator can be determined by comparing coloration of the test tool mentioned above after a certain period of time with a color tone of the standard color tone table prepared by similar procedures using solutions with known ionic strength or known specific gravity. Comparison can be made visually or measuring coloration of the test tool after a certain period of time (10 seconds to several minutes) through optical measurement of reflectivity by a known method.

Although the reagent composition of the present invention can be used most advantageously as a test strip, they may be used in a form of solution, powder, or tablet.

Other methods for detection by using a test strip or a tablet include a method wherein a liquid sample is dropped onto the test strip or tablet and coloration is observed visually or detected by optical measurement of reflectivity.

Hereinafter, the present invention will be described in more detail with reference to the examples.

EXAMPLE 1

Preparation of Test Strips 1.0 g of di(ethylhexyl) phosphate ($C_{16}H_{35}O_4P$) represented by the formula below as a phosphoric diester, 70 ml of 0.05M Tris HCl buffer (pH 8.0) as a pH buffering agent, 0.08 g of Bromothymol Blue and 0.008 g of Bromophenol Red as pH indicators, 0.6 g of Tris(hydroxyamino)methane, 30 ml of ethanol, and 2.0 g of Kollidon 30 as a binder, were mixed to prepare a reagent composition.

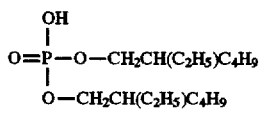

The reagent composition thus obtained was impregnated into filter paper (Whatman: 3 MM Chr) of 15 cm×15 cm and dried by blowing air at 80° C. for 10 minutes. The filter paper was cut into pieces of 5 mm×5 mm, which were stuck to the ends of white polyethylene terephthalate plates of 5 mm×60 mm by using colorless pressure sensitive adhesive double-coated tape, to prepare test strips.

Test Method

Aqueous solutions of sodium chloride with a specific gravity adjusted to each level of 1.000, 1.010, 1.020, and 1.030 were prepared as samples. The test strips previously prepared were immersed in the solutions for 2 seconds. After removed from the solutions, coloration of the test strips was observed visually and reflectivity was measured at 620 nm using a color-difference meter (Nippon Denshoku Kogyo K.K.: Σ-90).

Results

The test results are shown in the following table.

TABLE 1

| Salt concentration | Specific gravity | Coloration of the tes strip observed visually | Reflectivity measured by a color-difference meter (620 nm) |
|---|---|---|---|
| 0% | 1.000 | Blue | 20.2% |
| About 2% | 1.010 | Bluish green | 23.6% |
| About 4% | 1.020 | Green | 31.0% |
| About 6% | 1.030 | Yellow | 52.7% |

It is clear from the above results that the ionic strength and specific gravity of the liquid samples are well correlated with the reflection of the test strips.

EXAMPLE 2

Preparation of Test Strips 1.0 g of di(polyethyleneglycol-4-nonylphenyl) phosphate as a phosphoric diester, 0.6 g of 2-amino-2-methyl-1,3-propanediol as a pH buffering agent, 0.08 g of Bromothymol Blue as a pH indicator, and 100 ml of ethanol were mixed to prepare a reagent composition.

The reagent composition thus obtained was impregnated into filter paper (Whatman: 3 MM Chr) of 15 cm×15 cm and dried by blowing air at 80° C. for 10 minutes. The filter paper was cut into pieces of 5 mm×5 mm, which were stuck to the ends of white polyethylene terephthalate plates of 5 mm×60 mm by using colorless pressure sensitive adhesive double-coated tape, to prepare test strips.

Test Method

As in Example 1, aqueous solutions of sodium chloride with a specific gravity adjusted to each level of 1.000, 1.010, 1.020, and 1.030 were prepared. The test strips previously prepared were immersed in the above-mentioned solutions for 2 seconds. After removed from the solutions, coloration of the test strips was observed and reflectivity was measured.

Results

The test results are shown in the following table.

TABLE 2

| Salt concentration | Specific gravity | Coloration of the test strip observed visually | Reflectivity measured by a color-difference meter (620 nm) |
|---|---|---|---|
| 0% | 1.000 | Blue | 14.9% |
| About 2% | 1.010 | Bluish green | 20.5% |
| About 4% | 1.020 | Green | 28.6% |
| About 6% | 1.030 | Yellow | 34.6% |

It is clear from the above results that the ionic strength and specific gravity of the liquid samples are well correlated with the reflection of the test strips.

EXAMPLE 3

Preparation of Test Strips 1.0 g of di(hexadecyl) phosphate as a phosphoric diester, 0.6 g of 2-amino-2-methyl-1,3-propanediol as a pH buffering agent, 0.08 g of Bromothymol Blue as a pH indicator, and 100 ml of ethanol were mixed to prepare a reagent composition.

The reagent composition thus obtained was impregnated into filter paper (Whatman: 3 MM Chr) of 15 cm×15 cm and dried by blowing air at 80° C. for 10 minutes. The filter paper was cut into pieces of 5 mm×5 mm, which were stuck to the ends of white polyethylene terephthalate plates of 5 mm×60 mm by using colorless pressure sensitive adhesive double-coated tape, to prepare test strips.

Test Method

As in Example 2, aqueous solutions of sodium chloride with four different specific gravities were prepared. Coloration of the test strips was observed and reflectivity was measured.

Results

The test results are shown in the following table.

TABLE 3

| Salt concentration | Specific gravity | Coloration of the test strip observed visually | Reflectivity measured by a color-difference meter (620 nm) |
|---|---|---|---|
| 0% | 1.000 | Blue | 13.6% |
| About 2% | 1.010 | Bluish green | 17.4% |
| About 4% | 1.020 | Green | 25.0% |
| About 6% | 1.030 | Yellow | 30.3% |

It is clear from the above results that the ionic strength and specific gravity of the liquid samples are well correlated with the reflection of the test strips.

EXAMPLE 4

Preparation of Test Strips 1.0 g of di(ethylhexyl) phosphate as phosphoric diester, 0.6 g of 3-[4-(2-hydroxymethyl-1-piperadinyl] propanesulfonic acid as a pH buffering agent, 0.08 g of Bromophenol Blue as a pH indicator, 90 ml of ethanol, and 10 ml of purified water were mixed to prepare a reagent composition.

The reagent composition thus obtained was impregnated into filter paper (Whatman: 3 MM Chr) of 15 cm×15 cm and dried by blowing air at 80° C. for 10 minutes. The filter paper was cut into pieces of 5 mm×5 mm, which were stuck to the ends of white polyethylene terephthalate plates of 5 mm×60 mm by using colorless pressure sensitive adhesive double-coated tape, to prepare test strips.

Test Method

As in Example 3, aqueous solutions of sodium chloride with four different specific gravities were prepared. Coloration of the test strips was observed and reflectivity was measured.

Results

The test results are shown in the following table.

TABLE 4

| Salt concentration | Specific gravity | Coloration of the test strip observed visually | Reflectivity measured by a color-difference meter (620 nm) |
|---|---|---|---|
| 0% | 1.000 | Blue | 12.3% |
| About 2% | 1.010 | Bluish green | 19.0% |
| About 4% | 1.020 | Green | 28.7% |
| About 6% | 1.030 | Yellow | 33.5% |

It is clear from the above results that the ionic strength and specific gravity of the liquid samples are well correlated with the reflection of the test strips.

COMPARATIVE EXAMPLE 1

Preparation of Test Strips 100 ml of 0.03M phosphate buffer (pH 8.2) as a pH buffering agent and 0.1 g of Bromothymol Blue as a pH indicator were mixed to prepare a reagent composition.

The reagent composition thus obtained was impregnated into filter paper (Whatman: 3 MM Chr) of 15 cm×15 cm and dried by blowing air at 80° C. for 10 minutes. The filter paper was cut into pieces of 5 mm×5 mm, which were stuck to the ends of white polyethylene terephthalate plates of 5 mm×60 mm by using colorless pressure sensitive adhesive double coated tape, to prepare test strips.

Test Methods

As in Example 4, aqueous solutions of sodium hydrochloride with four different specific gravities were prepared. Coloration of the test strips was observed and reflectivity was measured.

Results

The test results are shown in the following table.

TABLE 5

| Salt concentration | Specific gravity | Coloration of the test strip observed visually | Reflectivity measured by a color-difference meter (620 nm) |
|---|---|---|---|
| 0% | 1.000 | Blue | 9.0% |
| About 2% | 1.010 | Bluish green | 12.8% |
| About 4% | 1.020 | Green | 15.4% |
| About 6% | 1.030 | Yellow | 18.5% |

In this example, although the ionic strength and specific gravity of the liquid samples were well correlated with the reflectivity of the test strips, sensitivity to coloration was lower than those in Examples 1–4.

The present invention is based on a principle quite different from conventional principles. The reagent composition of the present invention has high sensitivity, rapid reaction rate, with homogeneous development of color. Consequently, a novel tool for measurement of specific gravity of urine, which provide excellent measurement results, can be obtained.

What is claimed is:

1. A reagent composition for measurement of ionic strength of liquid samples containing at least one phosphoric diester, at least one pH buffering agent, and at least one pH indicator.

2. A reagent composition according to claim 1, wherein said phosphoric diester is a compound represented by the general formula (1) below:

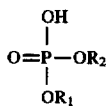 (1)

wherein, $R_1$ and $R_2$ in the formula (1), which may be different or the same each other, are organic groups selected from a group consisting of (a) straight or branched alkyl groups containing 4–20 carbon atoms, (b) phenyl groups, (c) phenyl groups substituted by straight or branched alkyl or alkoxyl groups, (d) benzyl groups, (e) benzyl groups substituted by straight or branched alkyl or alkoxyl groups, and (f) groups represented by the following formula(2):

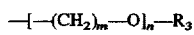 (2)

wherein, $R_3$ in the formula (2) is an organic group selected from a group consisting of any of the groups (a)–(e) shown for the formula (1) above, straight or branched alkylester residues and phenyl ester residues. m represents 2–6, and n represents an integer 1 or higher.

3. A reagent composition according to claim 1, wherein said pH buffering agent contains an organic base and is to be used in a pH range between 3.0 and 10.0.

4. A test tool for measurement of ionic strength of liquid samples containing the reagent composition according to claim 1.

5. A test tool according to claim 4, comprising a test strip prepared by impregnation of the reagent composition into absorptive carrier or coating or printing of the reagent composition onto a film.

6. A reagent composition according to claim 1, which is used for measurement of specific gravity of urine.

* * * * *